(12) United States Patent
Doucet

(10) Patent No.: US 12,207,999 B2
(45) Date of Patent: Jan. 28, 2025

(54) DEVICE FOR FACILITATING THE IMPLANTATION OF A SURGICAL MESH

(71) Applicant: SOFRADIM PRODUCTION, Trevoux (FR)

(72) Inventor: Genevieve Doucet, Frans (FR)

(73) Assignee: SOFRADIM PRODUCTION, Trevoux (FR)

( * ) Notice: Subject to any disclaimer, the term of this patent is extended or adjusted under 35 U.S.C. 154(b) by 379 days.

(21) Appl. No.: 17/702,738

(22) Filed: Mar. 23, 2022

(65) Prior Publication Data

US 2022/0304793 A1 Sep. 29, 2022

(51) Int. Cl.
*A61F 2/00* (2006.01)

(52) U.S. Cl.
CPC .... *A61F 2/0063* (2013.01); *A61F 2002/0068* (2013.01); *A61F 2002/0072* (2013.01)

(58) Field of Classification Search
CPC ............ A61F 2/0063; A61F 2002/0068; A61F 2002/0072
See application file for complete search history.

(56) References Cited

U.S. PATENT DOCUMENTS

| | | | | |
|---|---|---|---|---|
| 9,839,505 | B2 * | 12/2017 | Romuald | ............... A61F 2/0063 |
| 2012/0165937 | A1 * | 6/2012 | Montanari | ............... A61L 31/14 606/151 |
| 2012/0259348 | A1 | 10/2012 | Paul | |
| 2013/0172915 | A1 * | 7/2013 | Thomas | ................ A61F 2/0063 606/151 |
| 2013/0331792 | A1 * | 12/2013 | Karp | ..................... A61B 17/205 604/174 |
| 2014/0257348 | A1 * | 9/2014 | Priewe | .................. A61F 2/0063 606/151 |
| 2015/0073473 | A1 * | 3/2015 | Broom | ............. A61B 17/06166 606/228 |
| 2016/0151139 | A1 | 6/2016 | Pankratz et al. | |

FOREIGN PATENT DOCUMENTS

WO 2011026987 A1 3/2011

OTHER PUBLICATIONS

PCT Search Report and Written Opinion issued in PCT Application No. PCT/IB2022/052661 dated Jun. 3, 2022.

* cited by examiner

*Primary Examiner* — Jing Rui Ou
(74) *Attorney, Agent, or Firm* — Weber Rosselli & Cannon LLP

(57) ABSTRACT

The present invention relates to a device (10) for facilitating the implantation of a surgical mesh (1) having at least one barbed face (2), said device comprising:
- said surgical mesh (1),
- at least one biocompatible film (11, 11a, 11b) shaped and dimensioned to at least partially cover said barbed face (2),
- at least one cable (12) arranged to removably attach said film (11, 11a, 11b) to said barbed face (2) of said mesh (1).

18 Claims, 5 Drawing Sheets

[Fig. 1]
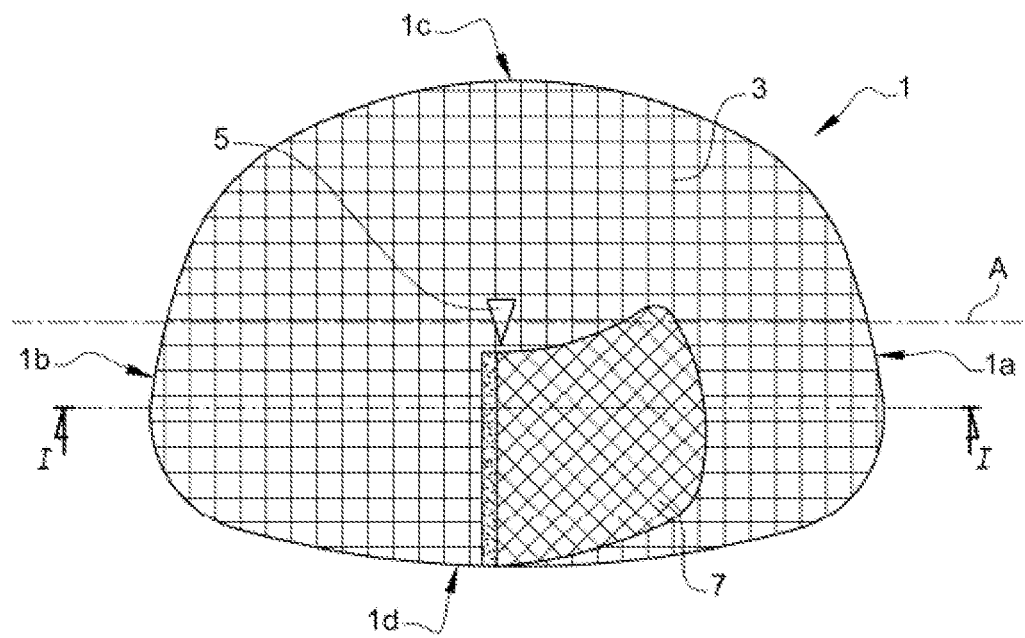
[Fig. 2]
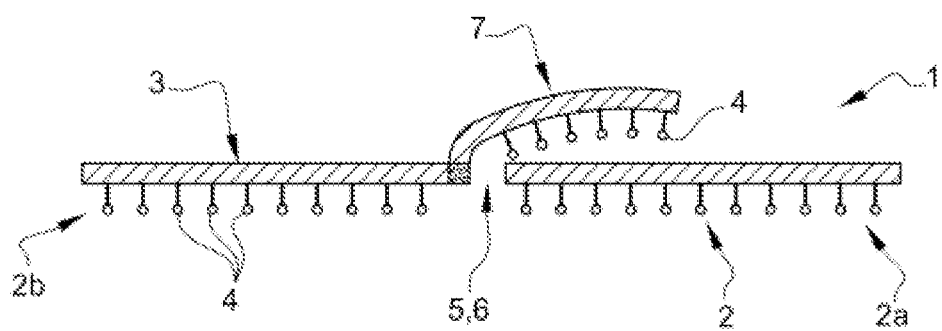

[Fig. 3]
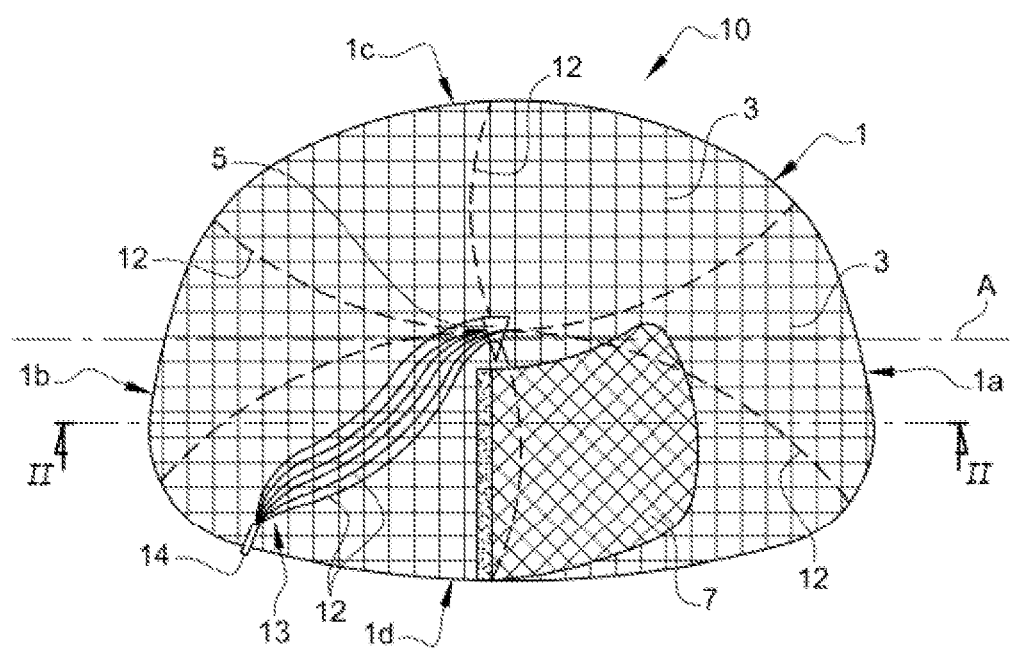
[Fig. 4]
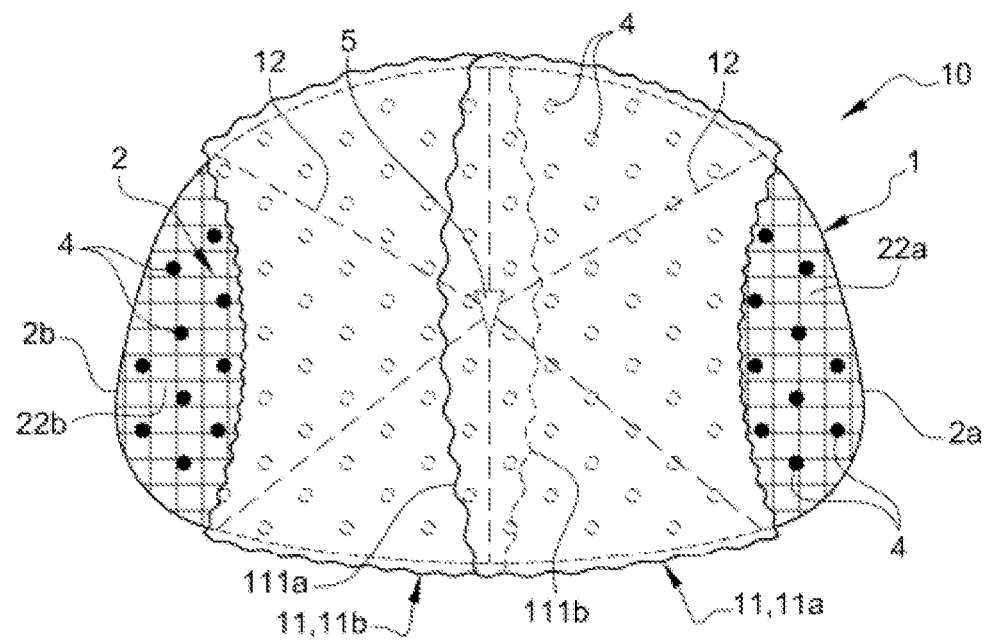

[Fig. 5]
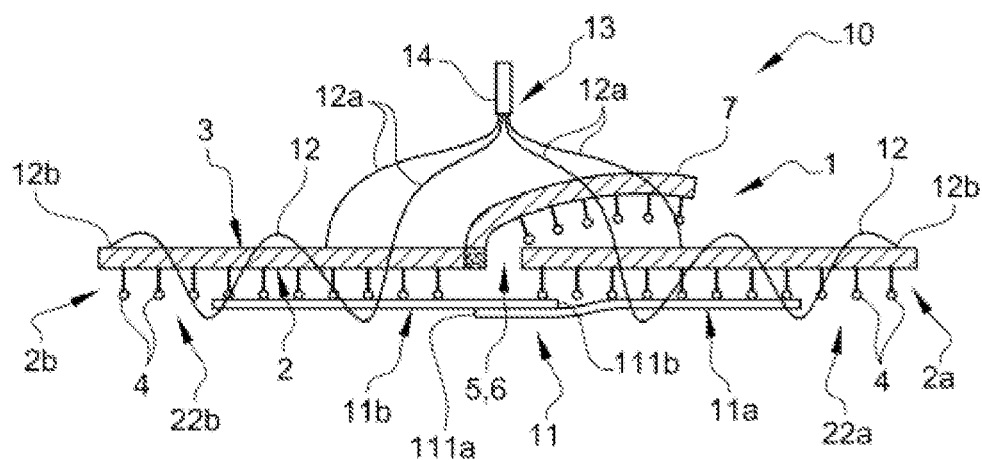
[Fig. 6]
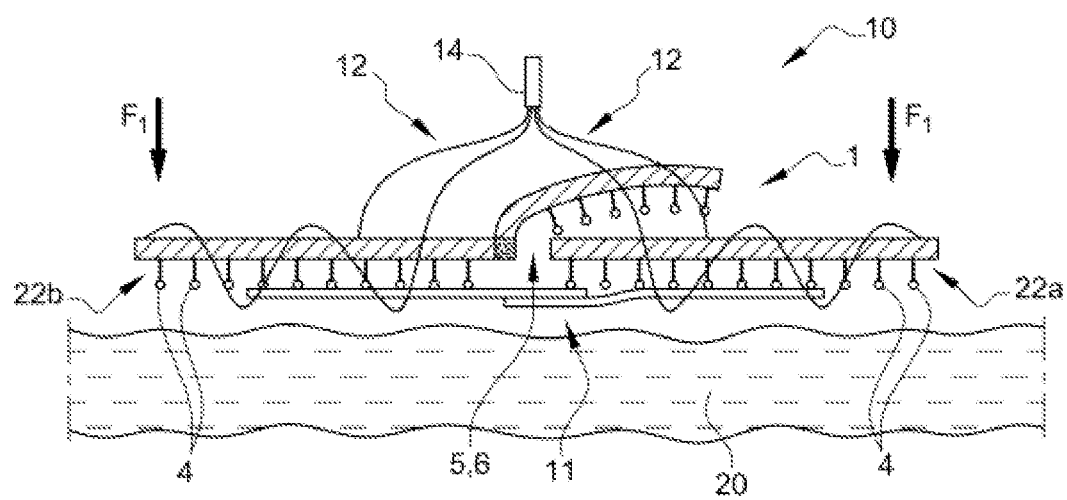

[Fig. 7]
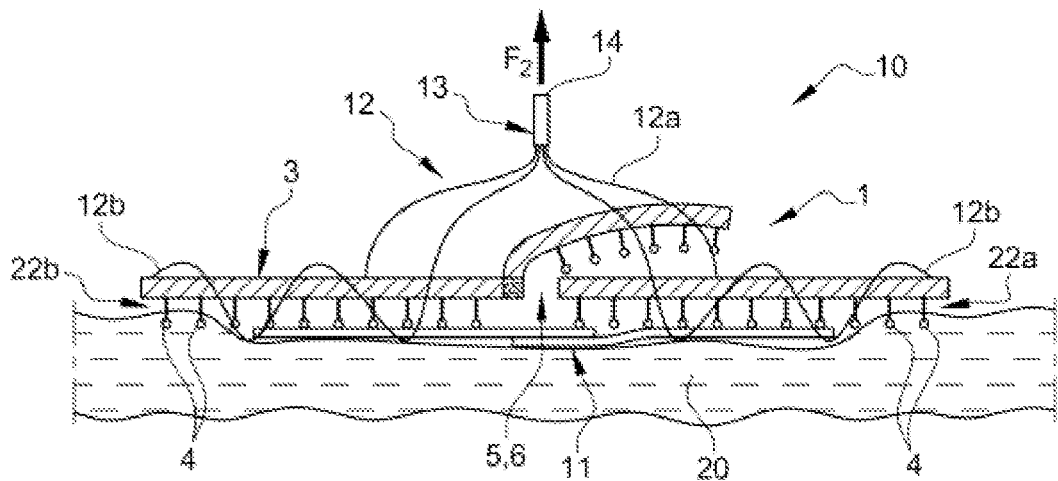
[Fig. 8]
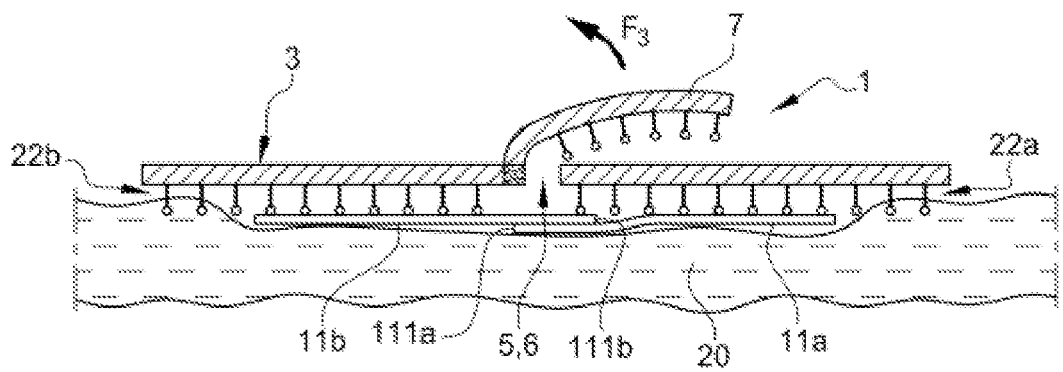
[Fig. 9]
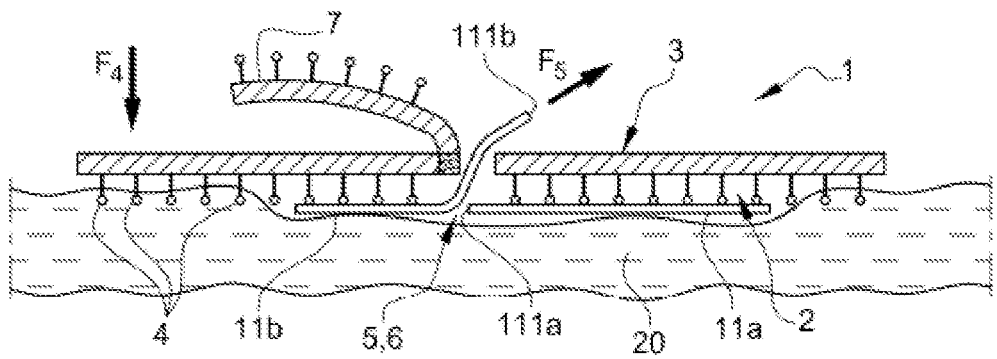

[Fig. 10]
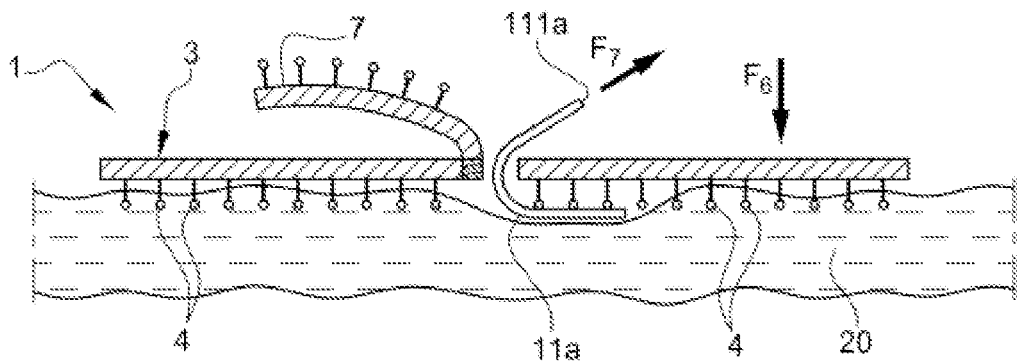
[Fig. 11]
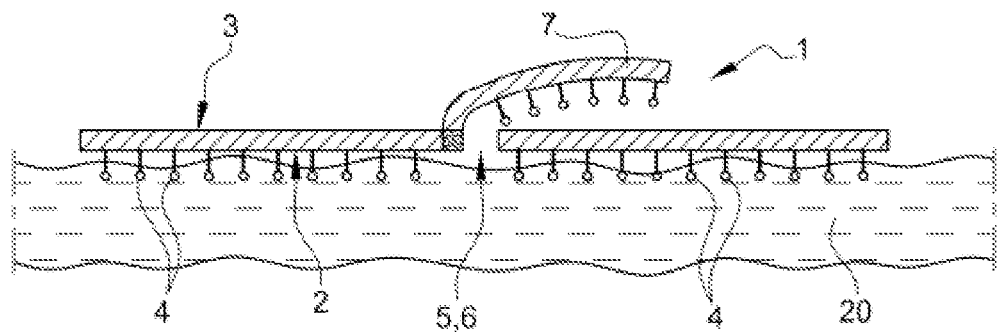
[Fig. 12]
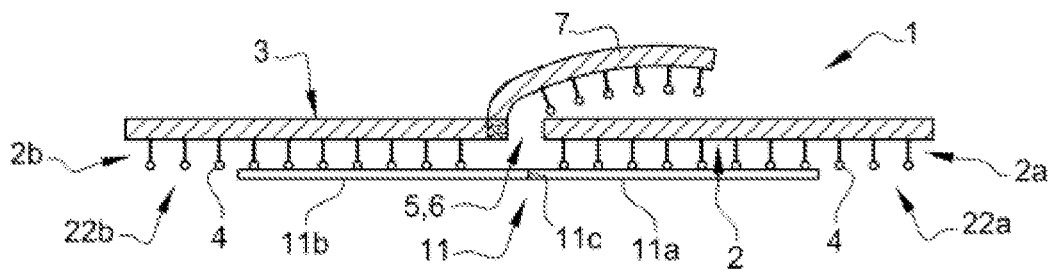
[Fig. 13]
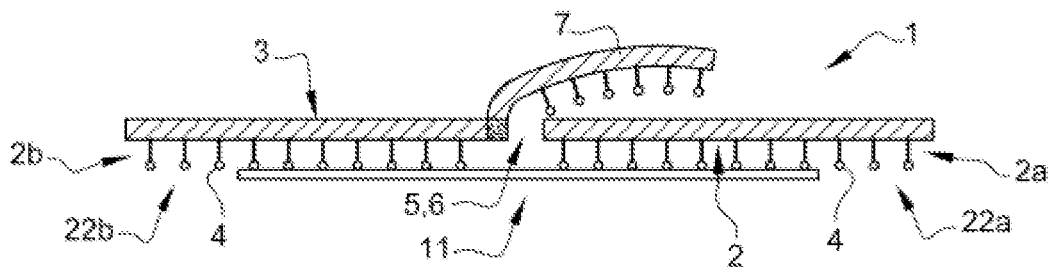

DEVICE FOR FACILITATING THE IMPLANTATION OF A SURGICAL MESH

CROSS-REFERENCE TO RELATED APPLICATIONS

This application claims the benefit of and priority to French Patent Application Serial No. 12102931 filed on Mar. 24, 2021, the disclosures of which is hereby incorporated by reference in their entirety.

The present invention relates to a device for facilitating the implantation in a patient's body of a surgical mesh provided with barbs on at least one of its faces. Such a mesh may be used for producing tissue-reinforcing prostheses for the treatment of hernias. The device of the invention is particularly useful in the treatment of inguinal hernia, where the mesh is preferably introduced in the patient's body via classical open surgery.

Tissue-reinforcing prostheses, for example prostheses for reinforcing the abdominal wall, are widely used in the surgical field. These prostheses are intended to treat hernias by temporarily or permanently reinforcing or filling a tissue defect. These prostheses are generally made of a biocompatible surgical mesh and can have a number of shapes, for example rectangular, circular or oval, depending on the anatomical structure to which they are to be fitted. Surgical meshes may be made of non-biodegradable yarns, or of biodegradable yarns, or of a combination of non-biodegradable and biodegradable yarns, depending on whether they are intended to remain permanently in the body of the patient or on the contrary to disappear after having carried out their reinforcing role while cell colonization takes place and tissue rehabilitation takes over.

Surgical meshes may comprise an arrangement of yarns, such as a knit, a woven fabric or non-woven fabric. They further may comprise barbs protruding outwards from one face, sometimes from both faces: these barbs constitute hooks that are able to fix themselves either in another mesh, belonging to the same prosthesis or not, or directly in the biological tissues, for example the abdominal wall.

Having a mesh provided with barbs on at least one of its faces provides several advantages. Thanks to the presence of barbs, the mesh may directly grip to the biological tissues and may be fixed thereon without having to use conventional attaching means such as tacks, staples, sutures or glue. Indeed, conventional attaching means such as tacks, staples, sutures and glue may be traumatizing for the biological tissues and be a source of chronic pain. Tacks, staples and sutures may also cause tensions in the biological tissues and/or tearing in the mesh. When a mesh provided with barbs is fixed to biological tissues, since the barbs are usually located on the whole surface of the face of the mesh, an optimal distribution of the forces over the whole mesh surface is obtained. This is an advantage over the fixation with tacks, staples or sutures of a mesh free of barbs, where the forces are concentrated at the fixation points, thereby possibly causing tearing of the mesh and potential discomfort for the patient.

Despite their advantages, surgical meshes provided with at least one barbed face may leave the surgeon with some negative perceptions, those negative perceptions making such surgical meshes challenging to implant.

Indeed, when a surgical mesh having at least one barbed face is conveyed to the implantation site, it may happen that the barbs stick to the tissues adjacent the implantation site, making it difficult to bring the surgical mesh up to the implantation site without possibly damaging the adjacent tissues, and/or the surgical mesh itself. The introduction phase of the surgical mesh is therefore not rendered comfortable for the surgeon.

Another drawback that may be encountered with surgical meshes having barbs is that the barbs make the mesh difficult to reposition once at the implantation site. Indeed, once a surgical mesh is conveyed up to an implantation site, it may happen that the surgeon wishes to try various locations and/or positioning of the mesh with regards to the surrounding tissues so that the mesh is able to ensure its function properly once fixed. The fact that the barbs make it difficult to detach and re-attach the mesh to biological tissues may render this positioning step challenging for the surgeon.

Moreover, the barbs may grip to the mesh itself when the mesh is folded, thereby hindering the subsequent deployment of the mesh and its positioning.

Thus, there remains a need for a device for facilitating the implantation of a surgical mesh having at least one barbed face, where such device would allow introducing the surgical mesh without damaging the barbs and/or the surrounding biological tissues and would further enable positioning and repositioning of the surgical mesh once said mesh has reached the implantation site.

A first aspect of the invention is a device for facilitating the implantation of a surgical mesh having at least one barbed face, said device comprising:
  said surgical mesh,
  at least one biocompatible film shaped and dimensioned to at least partially cover said barbed face,
  at least one cable arranged to removably attach said film to said barbed face of said mesh.

In the device of the invention, the biocompatible film covers the majority, in embodiments it covers all, the barbs present on the barbed face of the mesh. When the surgical mesh is conveyed to the implantation site, the surrounding biological tissues are therefore protected from the barbs, as they are mainly in contact with the surface of the biocompatible film, said surface being smooth and non-traumatizing. As a consequence, the surgeon does not have to face a situation where the surgical mesh becomes entangled in the surrounding tissue and where such tissues are damaged.

When the surgical mesh has reached the implantation site, the surgeon may easily manipulate the surgical mesh so as to try various positions of said mesh, as the biocompatible film, which is linked to the barbed face, is still covering the majority of the barbs, thereby continuing protecting the surrounding biological tissues. When a part of the barbed face of the surgical mesh is not covered, the surgeon may use this uncovered part to create a fixation point from where he may try various positions/orientations of the mesh.

Once the surgeon feels comfortable with a position of the surgical mesh, he may decide to remove the cable attaching the biocompatible film to the surgical mesh. Once this cable is removed, the surgeon may remove the biocompatible film as such. As appears from the present description, the biocompatible film and the cable(s) removably attaching said biocompatible film to the barbed face of the surgical mesh are not intended to remain in the patient's body. The biocompatible film and the cables are removed once the surgical mesh is correctly positioned. Once the biocompatible film and the cable(s) are removed, the barbs are allowed to grip the surrounding biological tissue and they can perform their fixing function.

The device of the invention therefore allows improving the handling of the mesh as the mesh may be folded without creating issues with the barbs, such as entanglement of the barbs within the mesh. The device of the invention further allows the repositioning of the surgical mesh without impairing the gripping performance of said mesh, since the barbs are damaged neither during the transportation of the mesh to the implantation site nor by the biocompatible film itself.

Moreover, the device of the invention further allows protecting the surrounding biological tissues during the insertion of the mesh in the patient's body up to the implantation site. In addition, since all the elements of the device but the mesh are removed from the patient's body once the mesh is implanted, the device of the invention does not contribute to add foreign material intended to remain in the patient's body.

As appears from the above, the device of the invention allows the surgeon to choose the moment when she/he wants to engage the barbs in the surrounding tissue and thus fix the mesh. If needed, the surgeon may also decide to remove the device entirely and re-introduce it, before removing the cables and the film. Thanks to the device of the invention, there is no time limit for the surgeon to decide to activate the barbs by removing the film from the mesh.

The device of the invention comprises a surgical mesh having at least one barbed face. The surgical mesh is usually made of an arrangement of biocompatible yarns, which may be for example a knit, a woven fabric or a non-woven fabric, said arrangement of yarns defining two opposite faces of the mesh. The barbs are present on at least one face of the mesh, in particular on the face of the mesh which is intended to be fixed to the surrounding biological tissues when the mesh is implanted. In embodiments, the barbs may be present on both faces of the mesh.

The barbs are intended to grip the mesh to the surrounding biological tissues once the mesh is correctly positioned at the implantation site. As such, the barbs usually protrude outwardly from the face of the mesh, for example substantially perpendicularly to the face of the mesh. In order to obtain a homogeneous fixation, in which the forces are distributed on the whole surface of the mesh, the barbs are preferably positioned on the whole surface of the barbed face of the mesh, in a more or less regular manner.

The yarns and barbs of the surgical mesh of the device of the invention are made of biocompatible material which may be biodegradable or non-biodegradable.

In the present application, "biocompatible" is understood as meaning that the materials having this property can be implanted in the human or animal body.

All biocompatible materials may be synthetic or natural, biodegradable, non-biodegradable or a combination of biodegradable and non-biodegradable. The term "biodegradable" as used herein is defined to include both bioabsorbable and bioresorbable materials. By biodegradable, it is meant that the materials decompose, or lose structural integrity under body conditions (e.g. enzymatic degradation or hydrolysis) or are broken down (physically or chemically) under physiologic conditions in the body such that the degradation products are excretable or absorbable by the body.

Biodegradable materials suitable for the surgical mesh of the present invention may be selected from polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), poly(glycolide-caprolactone-lactide-trimethylene carbonate), copolymers thereof and mixtures thereof. The non-biodegradable materials suitable for the surgical mesh of the present invention may be selected from polyethylene terephthalate (PET), polyamides, aramids, expanded polytetrafluoroethylene, polyurethane, polyvinylidene difluoride (PVDF), butyl ester polymers, polyetheretherketone (PEEK), polyolefins (such as polyethylene or polypropylene), polyethers, copper alloys, silver or platinum alloys, medical grades of steel such as medical-grade stainless steel, and combinations thereof.

The barbs may be obtained by melting loops generated by a heat-fusible monofilament yarn used in the construction of the mesh. The generation of barbs from preliminary loops made of heat-fusible monofilament yarn is known and is described, for example in document WO01/81667.

The mesh may show any shape, such as rectangular, circular or oval, depending on the anatomical structure to which it is intended to be fitted.

In embodiments, the surgical mesh of the device of the invention has a globally oval shape defining a longitudinal axis and two opposed ends of said barbed face. The two opposed ends are substantially aligned on said longitudinal axis. Such an oval shaped mesh may be used in particular in the treatment of hernias.

In embodiments, the surgical mesh is intended to treat inguinal hernia. The mesh may therefore have a globally oval shape defining a longitudinal axis and two opposed ends of said barbed face and be further provided with a slit for allowing the passage of the spermatic cord. Such surgical meshes are known: they are usually oval shaped and the slit extends from a point substantially located at a center of the mesh up to the edge of the mesh, at a point substantially located at a middle of one of the long sides of the mesh.

In other embodiments, the mesh may further be provided with a flap, extending from the edge of the slit, said flap being intended to close the mesh around the spermatic cord once the mesh is implanted. Such a flap may further be intended to maintain the mesh in a closed configuration. For example, such a flap may itself be provided with barbs on one of its faces, preferably on its face looking towards the face of the mesh that is free of barbs. Meshes provided with a slit and a flap and intended to be used in the treatment of inguinal hernias are known and will not be further described herein. In such meshes, the barbed face is preferably the face of the mesh which is not provided with the flap.

The device of the invention further comprises a biocompatible film. The biocompatible film is shaped and dimensioned to at least partially cover the barbed face of the surgical mesh.

As seen above, the film is intended to cover the majority of the barbs during the time the surgical mesh is transported to the implantation site in the patient's body and during the spreading and positioning of the mesh at said implantation site.

The film is preferably non porous. This allows providing a perfect coverage of the barbs, and therefore an optimal protection with respect to the surrounding biological tissues during the insertion of the mesh in the patient's body. A smooth and slick surface of the film allows the film to slide over the biological tissues and facilitates the removal of the film from the patient's body at the end of the implantation procedure.

The film is preferably thin. As an indication, the film may show a thickness ranging from about 15 µm to about 25 µm. A thin film allows preventing an overloading of the mesh. It also allows maintaining a good touch of the mesh and the barbs by the surgeon's fingertips.

The film preferably shows a certain strength in order not to be torn apart when the surgical mesh is introduced and conveyed inside the patient's body. The film must also show a sufficient strength, so that the surgeon may pull on the film at the end of the implantation procedure in order to remove it from the implantation site, without tearing the film apart.

The film is made from a biocompatible material. The film may be made from biodegradable, non-biodegradable or a combination of biodegradable and non-biodegradable materials as listed above. The film is preferably obtained by lamination of the biocompatible material it is made of. Such a lamination process is well known and will not be further described herein.

In embodiments, the film is made from biodegradable materials only. This limits the potential negative consequence of some parts of the film being left within the patient's body after implantation of the mesh. For example, the film is made of poly(glycolide-caprolactone-lactide-trimethylene carbonate). The preparation of a copolymer composition of poly(glycolide-caprolactone-lactide-trimethylene carbonate) suitable for forming the film of the device of the invention is described in U.S. Pat. No. 6,235,869.

In embodiments, the film may be shaped and dimensioned so as to cover the entire surface of the barbed face of the mesh. In such a case, the totality of the barbs present on the barbed face are covered by the film.

In embodiments where the mesh has a globally oval shape defining a longitudinal axis and two opposed ends of the barbed face, the film is shaped and dimensioned to leave at least a portion of one of said ends of said barbed face uncovered. The uncovered portion of an end of the barbed face allows the surgeon creating a first fixation point in the biological tissues, once the mesh is at the implantation site, by attaching the barbs present on said uncovered end portion to the surrounding biological tissues. This first fixation point enables the surgeon to try different positions and/or orientations for the mesh, while the film is still attached to the barbed face, before deciding on a final position. The presence of the film on the barbed face but the uncovered end portion thereof allows an easy handling of the mesh and a smooth and facilitated movement of the mesh within the biological tissues when the surgeon changes the position/orientation of said mesh. This first fixation point may be definitive if the surgeon has reached a position/orientation of the mesh he is comfortable with. Alternatively, since the uncovered end portion of the barbed face has a limited surface on which only a few barbs are present, this first fixation point may be temporary if the surgeon eventually decides to detach the barbs of the uncovered portion of the barbed face from the biological tissues and re-attach these barbs at a different location. For attaching, detaching and/or re-attaching the barbs of the uncovered end portion of the barbed face to/from the surrounding biological tissue, the surgeon simply needs to push, alternatively pull, on the face of the mesh which is free of barbs, in the region of the uncovered end of the barbed face.

In further embodiments, where the mesh has a globally oval shape defining a longitudinal axis and two opposed ends of the barbed face, the film is shaped and dimensioned to leave portions of both ends of said barbed face uncovered. Having uncovered portions of the barbed face at the two ends of the mesh allows the surgeon creating a preliminary fixation of the mesh to the surrounding biological tissues, before removing the film. Indeed, by pushing on both ends of the mesh in the direction of the biological tissues, the barbs present on the uncovered portions of the barbed face penetrate inside the biological tissue and perform a partial anchoring of the mesh in these tissues. As will appear more clearly in the detailed description below, such a preliminary anchoring of the mesh in the biological tissue will facilitate the removal of the film and of the cables attaching said film to the barbed face of the mesh.

In addition, in order to be removed from the implantation site easily, the film preferably shows a good flexibility and a good tear resistance. Indeed, although the strength of the film is likely to help limiting the creasing of the mesh, the film should anyway not add excessive rigidity to the mesh, as the mesh must be manipulated and folded easily. The film preferably shows a flexibility allowing it to be folded easily when it is separated from the mesh at the end of the implantation procedure.

In embodiments, wherein said mesh has a globally oval shape defining a longitudinal axis and two opposed ends of said barbed face, said mesh being further provided with a slit for allowing the passage of the spermatic cord in the treatment of inguinal hernia, said film shows a flexibility allowing it to be folded to pass through said slit once said film is detached from said barbed face.

Films showing a flexibility and a tear resistance suitable for the device of the invention may in particular be obtained via lamination of poly(glycolide-caprolactone-lactide-trimethylene carbonate).

In embodiments, the film is obtained by lamination of poly(glycolide-caprolactone-lactide-trimethylene carbonate). The preparation of such a film is for example described in document EP 3 106 185 B1. Such a film shows a flexibility allowing it to be folded easily and facilitating its removal from the implantation site.

In embodiments, the film is provided with a precut line, said precut line being substantially aligned on said slit. Such a precut line allows the surgeon to easily separate the film in two parts at the time he wishes to remove the film from the implantation site. As will appear from the detailed description below, the fact that the precut line is aligned on the slit of the mesh facilitates the grasping of each part of the film, through said slit, either by the surgeon's fingers or by any grasping tool.

In embodiments, the film is formed of two portions of film, each portion of film substantially covering a half of the mesh and having a central edge substantially aligned on said slit. In embodiments, the central edge of a portion of film overlaps the central edge of the other portion of film. In such embodiments, the surgeon needs not separate the film in two parts as the film is initially under the form of two portions. Such embodiments therefore facilitate the removal of the film at the end of the implantation procedure. The fact that a central edge of a portion of film overlaps the central edge of the other portion of film facilitates the grasping of each portion of film by the surgeon, as the overlap provides for a greater surface of film portion likely to be grasped, close to the edge of the film, in the vicinity of the slit of the mesh.

The device of the invention further comprises at least one cable arranged to removably attach the film to the barbed face. The cable may be any flexible and elongate structure capable of removably attaching the film to the barbed face, in particular as described herein. For example, the cable may be selected from a thread, a cord, a yarn, a wire, a tube and combinations thereof.

Preferably, the device comprises a plurality of cables arranged to removably attach the film to the barbed face.

The cables are made of biocompatible material, which may be biodegradable or non biodegradable. All biocompatible materials, as described above for the barbs and yarns of the surgical mesh, are suitable for making the cables.

The cables may be multifilament yarns, monofilament yarns or a combination of multifilaments yarns and monofilament yarns. In embodiments, the cables are monofilament yarns. Monofilament yarns allow preventing all entanglement between the cables and the barbs of the mesh.

The cables may further be colored: colored cables may be more easily spotted and differentiated from the mesh by the surgeon at the implantation site. In embodiments, cables of different colors may be used. Such an embodiment may be useful to distinguish some cable(s) from the other(s) if need be, for example to indicate to the surgeon a cable that should be removed in the first place.

In embodiments, the cables are monofilament yarns made of polyethylene terephthalate (PET).

The film is removably attached to the barbed face of the mesh by means of the film and the mesh being sewn together by the cables, in such a way that simply pulling on some of the cables will result in the cables being separated from the film and the mesh. The separation of the cables from the film and the mesh will result in the film and the mesh being simply positioned side by side, with no more attaching means one to the other. The surgeon will then be able to easily separate the film from the mesh.

In embodiments, the film is removably attached to the barbed face of the mesh by means of each cable simply crossing the two layers formed by the film and the mesh up and down, one or several times, without forming any knot. The friction between the cable and the film and the mesh causes the film and the mesh to be maintained together without the help of knots. Therefore, simply pulling on each cable in order to overcome said friction allows the cable to be removed from the two layers formed by the film and the mesh. The surgeon does not need to cut or to untie a knot in order to remove each cable.

In embodiments, a plurality of cables may be used, with each cable oriented radially, from a center of the mesh towards an edge of the mesh, without interacting with the other cables. Such a radial arrangement of the cables allows perfectly flattening the film and connecting the film to the barbed face of the mesh. In addition, the fact that the cables extend in the direction of the edge of the mesh without forming any knot allows the surgeon to trim the mesh if required, and if necessary, cut the distal end of the cable during this trimming step without impairing the connection between the film and the mesh.

In the present document, the distal end of a component is to be understood as meaning the end furthest from the user's hand and the proximal end is to be understood as meaning the end closest to the user's hand. In a radial arrangement of the cables as herein described, the proximal end of the cable is the end of the cable located at a center of the mesh, whereas the distal end of the cable is the end of the cable located in the direction of the edge of the mesh.

The radial arrangement of the cables therefore allows the mesh to be trimmed without losing the connection between the film and the barbed face of the mesh.

In embodiments, the distal end of each cable ends up on the face of the mesh which is not covered by the film. This allows maintaining a smooth surface of the film.

In embodiments, all the proximal ends of the cables are gathered together in a central tail that extends from a center of the mesh outwardly from the face of the mesh that is not covered by the film. The cables may be arranged under the form of a braid at a proximal end of the central tail in order to provide the surgeon with an easy-to-grasp element. The surgeon simply needs to pull on the braid to be sure to remove all the cables from the mesh and the film.

In alternative embodiments, a plurality of cables may be used, with the cables organized differently than according to a radially arrangement: the cables may for example extend in various directions on the surface of the mesh, and/or come linearly from one edge of the mesh, etc. . . . .

The invention and the advantages arising therefrom will clearly emerge from the detailed description that is given below with reference to the appended drawings as follows:

FIG. 1 is a top view of a surgical mesh on its own,

FIG. 2 is a cross section view of the surgical mesh of FIG. 1 taken along plane I-I, FIG. 3 is a top view of an embodiment of the device of the invention, FIG. 4 is a bottom view of the device of FIG. 3, FIG. 5 is a cross section view of the device of FIG. 3 taken along plane II-II, FIG. 6 is a cross section view showing the positioning of the device of FIG. 3 on the muscle to which it is intended to be fixed, FIG. 7 is a cross section view showing the preliminary anchoring of the device of FIG. 3 and the removal of the cables, FIG. 8 is a cross section view showing the opening of the flap of the mesh of the device of FIG. 3, FIG. 9 is a cross section view showing the removal of a first portion of film of the device of FIG. 3, FIG. 10 is a cross section view showing the removal of a second portion of film of the device of FIG. 3, FIG. 11 is a cross section view showing the mesh of the device of FIG. 3 fixed and anchored to the muscle, FIG. 12 is a partial cross section view of another embodiment of the device of the invention, FIG. 13 is a partial cross section view of another embodiment of the device of the invention.

With reference to FIGS. 1 and 2 is shown a surgical mesh 1 shaped and dimensioned to treat inguinal hernia. The mesh 1 is formed of an arrangement of biocompatible yarns defining two opposite faces of the mesh, a barbed face 2 and a face 3 free of barbs. The barbed face 2 comprises a plurality of barbs 4 which are regularly distributed on its surface. The barbs 4 are intended to penetrate the biological tissue to which the mesh 1 is intended to be fixed in a patient's body.

As shown in FIGS. 1 and 2, the mesh 1 has a globally oval shape defining a longitudinal axis A, two opposed ends (1a, 1b) and two opposed side edges (1c, 1d) of the mesh 1. The shape of the mesh 1 therefore further defines two opposed ends (2a, 2b) of the barbed face 2.

The mesh 1 is further provided with a central opening 5 and a slit 6 extending from this central opening 5 to one side edge 1d of the mesh 1. The slit 6 is intended to allow the passage for the spermatic cord once the mesh 1 is implanted. The mesh 1 is also provided with a flap 7, extending from an edge of the slit 6 outwardly from the face 3 of the mesh which is free of barbs. As shown in FIG. 2, the flap 7 is provided with barbs 4 on its face directed towards the face 3 of the mesh free of barbs. The flap 7 is intended to close the mesh 1 around the spermatic cord once the mesh 1 is implanted. The barbs 4 of the flap 7 may then help maintaining the mesh 1 in a closed configuration.

With reference to FIGS. 3-5 is shown a device 10 of the invention. The device 10 comprises the mesh 1 of FIGS. 1-2 and a biocompatible film 11, which is formed of two portions (11a, 11b) of film, said film 11 partially covering the barbed face 2 of the mesh 1.

With reference to FIG. 4, the film (11, 11a, 11b) covers a majority of the barbs 4 present on the barbed face 2 but is shaped and dimensioned to leave some portions (22a, 22b) of ends (2a, 2b) of barbed face 2 uncovered. As will appear in the description of the implantation procedure below, uncovered portions 22a and 22b of barbed face 2 will allow the surgeon creating preliminary fixation points when positioning the mesh 1 with respect to the biological tissues.

As shown in FIG. 5, a first portion 11b of film 11 covers substantially a half of the barbed face 2, except from uncovered portion 22b of first end 2b, and a second portion 11a of film 11 covers substantially the other half of the barbed face 2, except from uncovered portion 22a of second end 2a. Each portion (11a, 11b) of film 11 has a central edge (111a, 111b) substantially aligned on the slit 6. Anyway, as seen in FIG. 5, the central edge 111b of first portion 11b of film 11 overlaps the central edge 111a of second portion 11a of film 11. Such an overlap provides for a significant part of film 11 to be grasped by the surgeon at the time of removal of the film 11 from the implantation site.

In an alternative embodiment shown in FIG. 12, the film 11 is made of only one piece of film provided with a precut line 11c. The precut line 11c is substantially aligned on the slit 6. The precut line 11c allows the surgeon to easily separate the film 11 in two portions (11a, 11b) when he is ready to remove the film 11 from the implantation site, once the mesh 1 is correctly positioned. The surgeon will then remove one portion of film after the other, by passing those portions of film through the slit 6.

In another embodiment shown in FIG. 13, the film 11 is made of a single piece of film which will be removed by the surgeon by passing through the slit 6 of the mesh 1.

The film 11 is preferably non porous and may be made from biodegradable materials only. In addition, the film 11 has a flexibility allowing it to be folded so that the surgeon may convey the film 11 through the slit 6 of the mesh 1 when he wishes to remove the film 11 from the implantation site, once the film 11 is detached from the mesh 1.

In embodiments, the film 11 is obtained via lamination of poly(glycolide-caprolactone-lactide-trimethylene carbonate).

The device 10 of the invention further comprises a set of six cables 12 arranged to removably attach the film 11 to the barbed face 2 of the mesh 1.

In embodiments not shown, the device could comprise another number of cable(s) removably attaching the film to the mesh, like for example only one cable, or alternatively a set of four, five, seven, eight or more cables, as long as the film is maintained attached to the mesh in a removable manner.

The cables 12 are distributed radially over the mesh 1: in other words, each cable 12 extends from a center of the mesh 1, for example from the central opening 5 of the mesh 1, towards the edge of the mesh 1. In addition, each cable 12 crosses the two layers formed by the film 11 and the mesh 1 up and down, several times, without forming any knot. The film 11 is therefore sewn to the barbed face 2 of mesh 1 in a non-definitive manner. Indeed, it is the friction between the cables 12 on one end, and the film 11 and the mesh 1 on the other end, that causes a removable attachment of the film 11 to the mesh 1. The radial organization of the cables 12 further allows flattening the film 11. The sewing of the film 11 to the mesh 1 as described above has the consequence that none of the cable 12 interacts with the other cables. Each cable 12 may therefore be removed by simply pulling on its proximal end 12a with a force capable of overcoming the friction described above between the cable 12 and the film 11 and the mesh 1.

As seen in FIG. 5, for each cable 12, its distal end 12b is located on the face 3 of the mesh 1 which is free of barb. This allows preserving the smoothness of the film 11 when the device 10 is conveyed to the implantation site.

The proximal ends 12a of the cables 12 are all gathered together in a central tail 13 that extends from a center of the mesh 1 outwardly from the face 3 of the mesh 1 which is free of barbs. The cables 12 may be arranged under the form of a braid 14 at a proximal end of the central tail 13. Such a braid 14 provides for an easy-to-grasp element for the surgeon during the step of removal of the cables 12.

The cables 12 are made of biocompatible material. They may be colored so as to be easily identified by the surgeon at the implantation site. For example, the cables 12 may be PET monofilaments yarns.

The method for implanting the mesh 1 in the inguinal region of a patient using the device 10 of the invention will now be described with reference to FIGS. 6-11.

In FIGS. 6-11, for simplification purposes, the biological tissues to which the mesh 1 is intended to be fixed is schematized as tissue 20. This tissue 20 could be one of the muscles of the abdominal wall of the inguinal region, such as the psoas muscle of the transverse muscle, or may also represent the tissues covering the pubic bone.

The device 10 of the invention is conveyed to the implantation site in its configuration shown in FIG. 5, with the film 11 covering the majority of the barbs 4 present on the barbed face 2 of the mesh 1, only the barbs 4 present on uncovered portions (22a, 22b) of the barbed face 2 being left free. In this configuration also, the flap 7 of the mesh 1 covers the slit 6, and the film 11 is removably attached to the mesh 1 by means of the plurality of cables 12 sewing the film 11 to the mesh 1 as described above;

The presence of the film 11 allows transporting the device 10 through the surrounding biological tissues without damaging the barbs 4 and as a consequence without jeopardizing the gripping capacities of these barbs. The film 11 further allows protecting the surrounding biological tissues from being damaged by the barbs 4 during movement of the device 10.

With reference to FIG. 6, the device 10 is moved closed to the tissue 20, with the barbed face 2 of the mesh 1, substantially covered by the film 11, facing the tissue 20. Although not shown on this Figure for clarity's sake, the surgeon may open the flap 7 to position it correctly around the spermatic cord (not shown). When the surgeon is ready to try a first positioning for the mesh 1, he pushes on one or both of the uncovered portions (22a, 22b) of the ends (2a, 2b) of barbed face 2, as shown by arrows F1 of FIG. 6. On these uncovered portions (22a, 22b), the barbs 4 are left free and they can penetrate the tissue 20 to anchor partially the mesh 1 therein. Anyway, at this stage, the surgeon may still decide to change the position of the mesh 1, and to detach the uncovered portions (22a, 22b) from the tissue 20 in order to try a second positioning of the mesh 1 at a different location of tissue 20. The uncovered portions (22a, 22b) of the barbed face 2 therefore allow the surgeon creating preliminary fixation points until he reaches the positioning of the mesh he feels comfortable with, without being confronted to a situation where the barbs would become entangled with the mesh or with the surrounding biological tissues. The positioning step is therefore facilitated for the surgeon.

Once the surgeon is happy with the positioning of the mesh 1 and the barbs 4 present on the uncovered portions (22a, 22b) of the barbed face 2 of the mesh are anchored into the tissue 20 as shown in FIG. 7, the surgeon may decide to remove the elements of the device 10 which are not intended to remain in the patient's body.

In this view, the surgeon grasps the braid 14 provided at the proximal end of the central tail 13 and he pulls on this braid 14 in the direction of arrow F2 as shown in FIG. 7. Since the cables 12 simply cross the two layers formed by the film 11 and the mesh 1 without forming knots, and since their distal ends 12b are free, the surgeon can easily exert a pulling force sufficient for overcoming the friction between the cables 12 and the film 11 and the mesh 1. The cables 12 are therefore removed from device 10 and from the implantation site as shown in FIG. 8.

Still with reference to FIG. 8, the film 11 and the mesh 1 are now detached from one another and are simply positioned one next to the other. If necessary, the surgeon may then further open the flap 7 in the direction shown as arrow F3 in FIG. 8 to uncover the slit 6 of the mesh 1, so that he is able to more easily visualize the central edge 111b of the first portion 11b of film 11.

With reference to FIG. 9, the surgeon may then grasp the central edge 111b of the first portion 11b of film 11 and pull on this central edge 111b, as shown by arrow F5, so as to remove the first portion 11b of film from the implantation site by passing this first portion 11b of film 11 through the slit 6. The strength and the flexibility of the film allow it to be folded and to traverse the slit 6 without being torn apart. At the same time, the surgeon may apply a force shown by arrow F4 on the half of the mesh 1 which is freed from this portion 11b of film 11. The barbs 4 present on this part of the barbed face 2 of the mesh 1 are therefore caused to penetrate the tissue 20.

Once the first portion 11b of film 11 is removed, the surgeon is able to visualize the central edge 111a of the second portion 11a of film 11.

With reference to FIG. 10, the surgeon may then grasp the central edge 111a of the second portion 11a of film 11 and pull on this central edge 111a in the direction of arrow F7. Thanks to its flexibility, this second portion 11a of film 11 traverses the slit 6 and is removed from the implantation site without being torn apart. At the same time, the surgeon may apply a force shown by arrow F6 on the part of the mesh 1 not yet anchored to tissue 20. As the remaining barbs 4 of the barbed face 2 are freed from the second portion 11a of film 1, they are caused to penetrate the tissue 20.

With reference to FIG. 11, all the barbs 4 of the barbed face 2 of the mesh 1 have entered tissue 20 and the mesh 1 is perfectly anchored to tissue 20, without the need of additional conventional fixing means such as staples or sutures. Moreover, no other foreign material but the mesh is implanted, as the cables and the film of the device of the invention have been removed from the patient's body. In a final step (not shown), the surgeon may carefully close the flap 7 around the spermatic cord (not shown) and apply a pressure on the flap 7 in direction of the face 3 of the mesh 1 which is free of barbs, in order to grip the barbs of the flap 7 into said face 3, thereby ensuring that the mesh 1 is maintained in a closed configuration.

The device of the invention is therefore particularly useful for facilitating the implantation of a surgical mesh having a barbed face in a patient's body. The device of the invention allows inserting the mesh inside the patient's body and conveying the mesh up to the implantation site while preserving both the surrounding biological tissues and the gripping capacities of the barbs. The device of the invention further allows the surgeon to position and reposition the mesh easily and as many times as needed without damaging the tissues.

The invention claimed is:

1. A device for facilitating the implantation of a surgical mesh having at least one barbed face, the device comprising:
   the surgical mesh,
   at least one biocompatible film shaped and dimensioned to at least partially cover the barbed face, and
   at least one cable arranged to removably attach said film to said barbed face of said mesh.

2. The device of claim 1, wherein the film is non-porous.

3. The device of claim 1, wherein the film is made from biodegradable materials only.

4. The device of claim 1, comprising a plurality of cables arranged to removably attach said film to said barbed face of said mesh.

5. The device of claim 4, wherein the film is removably attached to the barbed face of the mesh by means of each cable simply crossing two layers formed by the film and the mesh up and down, one or several times, without forming any knot.

6. The device of claim 4, wherein each cable is oriented radially, from a center of the mesh towards an edge of the mesh, without interacting with the other cables.

7. The device of claim 6, wherein a distal end of each cable ends up on a face of the mesh which is not covered by the film.

8. The device of claim 6, wherein all the proximal ends of the cables are gathered together in a central tail that extends from a center of the mesh outwardly from a face of the mesh that is not covered by the film.

9. The device of claim 1, wherein said mesh has a globally oval shape defining a longitudinal axis and two opposed ends of said barbed face.

10. The device of claim 9, wherein said film is shaped and dimensioned to leave at least a portion of one of said two opposed ends of said barbed face uncovered.

11. The device of claim 10, wherein said film is shaped and dimensioned to leave portions of both of said two opposed ends of said barbed face uncovered.

12. The device of claim 11, wherein said mesh being intended to treat inguinal hernia, said mesh is further provided with a slit for allowing the passage of the spermatic cord.

13. The device of claim 12, wherein said mesh is further provided with a flap, extending from an edge of the slit, said flap being intended to close the mesh around the spermatic cord once the mesh is implanted.

14. The device of claim 12, wherein said film shows a flexibility allowing it to be folded to pass through said slit once said film is detached from said barbed face.

15. The device of claim 12, wherein said film is provided with a precut line, said precut line being substantially aligned with said slit.

16. The device of claim 12, wherein said film is formed of two portions of film, each portion of film substantially covering a half of the mesh and having a central edge substantially aligned with said slit.

17. The device of claim 16, wherein the central edge of a portion of film overlaps the central edge of the other portion of film.

18. The device of claim 1, wherein the film is obtained via lamination of poly(glycolide-caprolactone-lactide-trimethylene carbonate).

* * * * *